(12) United States Patent
Kadziauskas et al.

(10) Patent No.: US 6,261,297 B1
(45) Date of Patent: *Jul. 17, 2001

(54) THERMAL MODE PHACO APPARATUS AND METHOD

(75) Inventors: Kenneth E. Kadziauskas, Laguna Niguel; Paul W. Rockley, Newport Coast, both of CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/434,738

(22) Filed: Nov. 5, 1999

(51) Int. Cl.⁷ ........................................................ H61F 9/00
(52) U.S. Cl. ........................... 606/107; 606/159; 604/67; 604/31
(58) Field of Search .................................. 606/107, 159; 604/22, 31, 65, 66, 67, 118; 601/2

(56) References Cited

U.S. PATENT DOCUMENTS

| | | | |
|---|---|---|---|
| 3,693,613 | * 9/1972 | Kelman | 604/22 |
| 4,156,187 | * 5/1979 | Murry et al. | 604/22 |
| 5,139,509 | * 8/1992 | Fischer et al. | 606/107 |
| 5,154,696 | * 10/1992 | Shearing | 606/107 |
| 5,160,317 | * 11/1992 | Costin | 604/22 |
| 5,279,547 | * 1/1994 | Costin | 604/22 |
| 5,342,293 | * 8/1994 | Zanger | 604/22 |
| 5,520,633 | * 5/1996 | Costin | 604/22 |
| 5,569,188 | * 10/1996 | Mackool | 606/107 |
| 5,700,240 | * 12/1997 | Barwick, Jr. et al. | 604/22 |
| 5,733,256 | * 3/1998 | Costin | 604/22 |
| 5,766,146 | * 6/1998 | Barwick, Jr. | 604/28 |
| 5,865,790 | * 2/1999 | Bair | 604/22 |
| 6,083,193 | * 7/2000 | Kadziauskas et al. | 606/107 |

* cited by examiner

Primary Examiner—Pedro Philogene
(74) Attorney, Agent, or Firm—Walter A. Hackler

(57) ABSTRACT

Control apparatus for an ultrasonic phacoemulsification handpiece utilizes flow rates and temperature measurements as well as power provided to a handpiece for calculating an energy balance over a time interval and in response thereto, regulating power and/or fluid flow to and from the handpiece.

12 Claims, 2 Drawing Sheets

THERMAL MODE PHACO APPARATUS AND METHOD

The present invention is generally directed to apparatus and a method for controlling power delivery to an ultrasonic phacoemulsification handpiece as well as controlling fluid flow to and from an eye during ocular surgery with the phacoemulsification handpiece. More particularly, the invention is directed to apparatus and a method for controlling phaco power delivery and/or fluid flow based upon the amount of thermal energy delivered to an eye over a specific period of time.

Phacoemulsification of cataractic lenses is a medically recognized technique. The method generally includes making of a corneal incision and the insertion of a hand held surgical implement, i.e., handpiece, which includes a needle which is ultrasonically driven in order to emulsify the eye lens. Simultaneously, with this emulsification, a fluid is inserted for irrigation of the emulsified lens and a vacuum provided for aspiration of the emulsified lens and inserted fluids.

In order to maintain normal pressure within the eye, a balanced salt solution is provided as an irrigation fluid and typically supplied from an elevated chamber. Importantly, the irrigation and aspiration of fluid through the eye must be carefully monitored in order to maintain normal pressure within the eye during surgical procedures. For example, an underpressure condition may cause distortion of the eye which often may interfere with surgical procedures. On the other hand, overpressure may cause damage to the eye.

As hereinabove noted, pressure in the eye may be controlled by physical elevation of the source of irrigation fluid interconnected to the phacoemulsification handpiece. Aspiration of fluid is typically controlled through the use of peristaltic pump or the like.

It should be appreciated that the control of irrigation and aspiration fluids is a dynamic problem. For example, during surgical procedures, fragments of broken tissue may temporarily block an aspiration line or the handpiece. This may lead to a differential pressure which is typically accommodated by stopping or slowing aspiration flow through the regulation of the peristaltic pump connected to the aspiration line.

During aspiration of the lens and aspiration fluid, particles may restrict the aspiration flow from the eye through an aspiration port in the tip of the phacoemulsification handpiece. In order to clear this occlusion, vacuum levels may be increased to create a greater differential pressure across the occluding particle in an effort to move the particle downstream and away from the eye. Typically, particles require much higher force to start movement than it takes to continue movement of the particle to the peristaltic pump. Once a particle moves, it creates a subsequent volume of fluid to take up the space it once occupied. This volume may be momentarily larger than the volume of fluid in the eye, therefore, producing a momentary-dimpling of the eye.

It has been shown that the pressure sensing of this condition is well within the operation of the phaco machine.

However, of further consideration regarding the utilization of phacoemulsification handpiece, is the amount of power delivered to the lens by the handpiece in order to fragment the lens. If too much power is delivered to the handpiece, without concomitant fluid or cooling irrigation fluid, local temperatures of the eye may rise to a level causing localized trauma. On the other hand, the entire eye may be heated during the procedure within the anterior chamber which may cause damage. Thus, it is important to not only control the power delivery of a phacoemulsification handpiece, but to provide a means for calculating elevated anterior chamber temperatures in order to prevent any tissue damage due to excess delivered power. Such damage can occur within one to two seconds under adverse heating conditions.

It should be appreciated that in combination with the occlusion of the phacoemulsification needle, as hereinabove described, the fluid flowing from the eye can vary considerably. Thus, heat is not removed from the eye in a generally continuous basis, but, of course, is dependent upon the actual fluid flow as a function of time. Heretofore, consoles for providing irrigation fluid and power of an ultrasonic phacoemulsification handpiece and aspirating fluid from the eye during ocular surgery, have not taken into account energy and power considerations nor utilized same for controlling the operation of the phacoemulsification handpiece.

The present apparatus and method provide for such operation.

SUMMARY OF THE INVENTION

Control apparatus, by itself, or for use in a control console for providing irrigation fluid and controlling power to an ultrasonic phacoemulsification handpiece and aspiration from an eye during ocular surgery, generally includes a means for monitoring energy provided to the handpiece and means for monitoring energy removed from the eye by aspirated fluid. In connection therewith, a computer responsive to input from the means for monitoring power provided and removed, provides a means for calculating an energy balance over a time interval and, accordingly, regulating the power provided to the handpiece. The power may be regulated by changing the duty cycle thereof.

In addition, regulation of the fluid flow may also be performed in response to the energy balance calculation.

More particularly, the means for monitoring power removed from the eye may include a means for measuring the flow rate of the aspirated fluid and/or irrigation fluid and may further include a means for measuring a temperature difference between the irrigation fluid and the aspirated fluid.

Additionally, output means, which is responsive to the computer means, may provide an indication of eye temperature based upon the energy balance. Specifically, the output means may provide an alarm at a selected eye temperature level. This enables a continuous monitoring of the eye temperature and, in addition, either visual or audible alarm, may be provided at any selected level in order to attract attention to an energy imbalance in order to prevent thermal damage to eye tissue.

Correspondingly, a method for regulating fluid flow and power to an ultrasonic phacoemulsification handpiece, includes the steps of monitoring power provided to the handpiece, monitoring power removed from the eye by the aspirated fluid and calculating, in response to input from the steps of monitoring the power provided and the power removed, an energy balance over time interval, with subsequent regulation of the power provided to the handpiece and fluid flow of the irrigation fluid and aspiration fluid.

BRIEF DESCRIPTION OF THE DRAWINGS

The advantages and features of the present invention will be better understood by the following description, when considered in conjunction with the accompanying drawings, in which.

DETAILED DESCRIPTION

Figure 1:
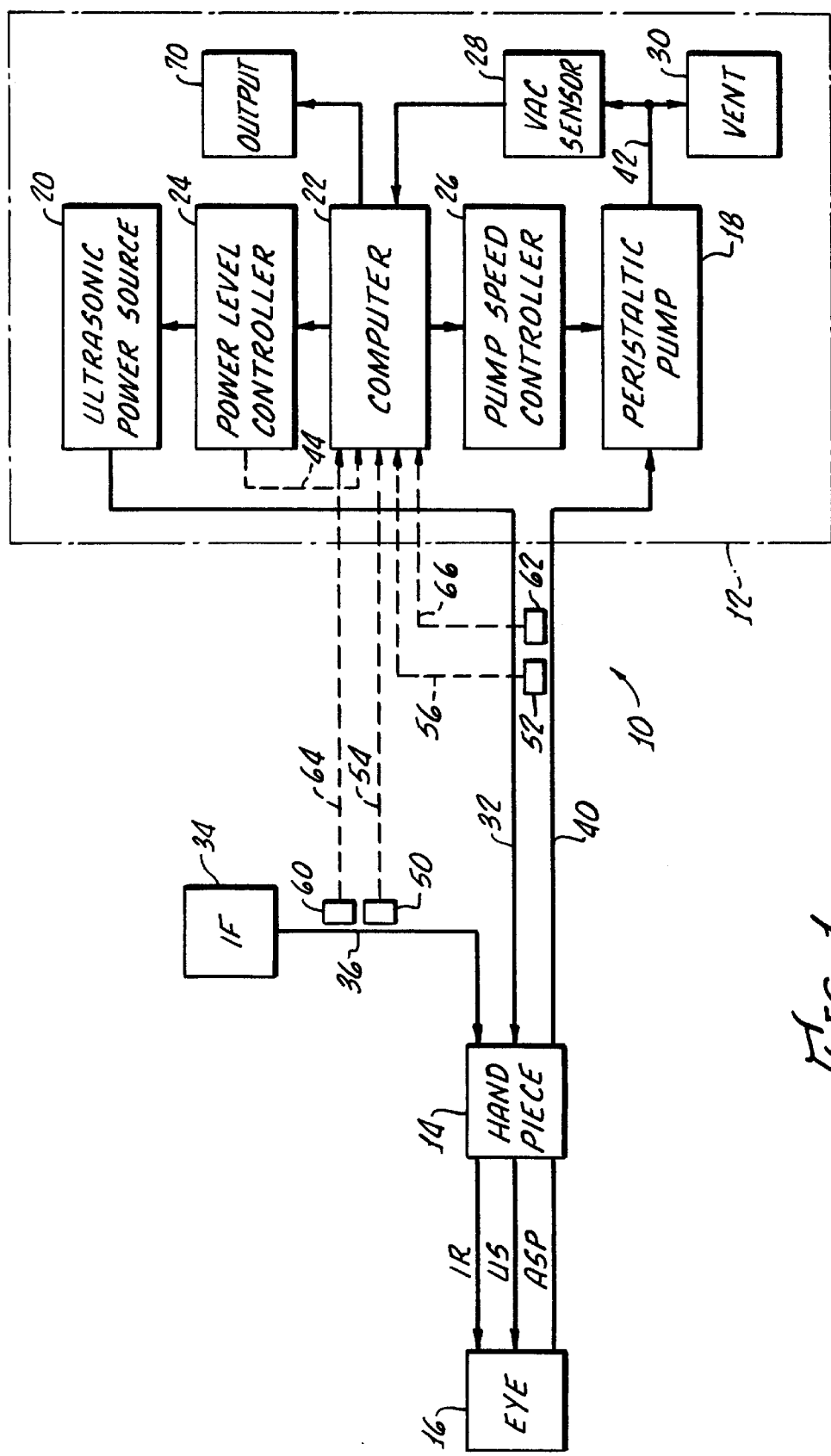
FIG. 1 is a block diagram of control apparatus in accordance with the present invention.

Turning now to FIG. 1, there is shown, in functional block diagram form, a phacoemulsification system. The system 10 includes a control console 12 for providing irrigation fluid and power to an ultrasonic phacoemulsification handpiece 14, and aspirating fluid from an eye 16 during ocular surgery. The console 12 includes a variable speed peristaltic pump 18 which provides a vacuum source, a source of pulsed ultrasonic powers 20, and a microprocessor computer 22, an ultrasonic power level controller 24 and a pump speed controller 26. A vacuum sensor 28 provides input to the computer 22 representing a vacuum level on an input side of the peristaltic pump 18. Suitable venting is provided by vent 30. This apparatus and availability is described in greater detail in U.S. Pat. No. 5,700,240 which is incorporated herewith in its entirety for describing a control console 12 suitable for use in the present invention.

The console 12 supplies ultrasonic power on line 32 to the handpiece 14 and an irrigation of fluid source 34 is coupled to the handpiece 14 through line 36. The irrigation fluid and ultrasonic power applied by the handpiece 14 to a patient's eye, which is indicated diagrammatically by block 16. Aspiration of the eye 16 is achieved through line 40.

The power level controller 24 provides a means from monitoring power provided to the handpiece 14 by the console 12 and an output indicating a signal corresponding to the power provided to the handpiece 14 may be separately imputed to the computer 22 as indicated by the dashed line 44.

Any suitable temperature sensors 50, 52 connected to the computer 22 by lines 54, 56 and flow sensors 60, 62 interconnected to the computer by lines 64, 66, respectively, provide a means for monitoring power removed from the eye 16 by aspirated fluid. The temperature sensors 50, 52 and flow sensors 60, 62 may be of any suitable type. Since the flow rates and temperature of the aspiration and irrigation fluids are known, as well as the power provided to the handpiece, an energy balance can be calculated by the computer.

Energy balance, as the term is used herein, assumes flow through the handpiece which is not chemically changed, i.e., no chemical reaction of the fluid occurs within the eye 16 or the handpiece 14.

The microprocessor computer 22 accordingly is capable of determining cumulative phaco power delivered over a period of time as well as the cumulative fluid removed from the eye by the peristaltic pump 16. Under the further assumption of a tight wound and minimal fluid leakage, aspiration flow and irrigation fluid are equivalent in the eye system. Therefore, a correlation is established between the fluid flow, phaco power and heat generation in the handpiece 14. In fact, empirically, the flow rate of irrigation/aspiration fluids may be utilized to determine the eye temperature given the heat input by the phaco power provided by the handpiece. In this instance, the fluid temperatures need not be continually measured or monitored.

As hereinabove noted, decreasing flow coupled with phaco power deployment over extended time may result in burns or chamber heating.

The computer 22 utilizes either a look-up table or algorithm to determine an energy balance and whether the control console 12 should continue with existing power and fluid settings or switch to modified settings which may be preprogrammed by a user. In addition, the computer may modulate the phaco power level or duty cycle based upon the level of a "heat factor" determined by the energy balance.

In addition, the computer 22 may provide an output indicated by the block 70, which may be of any suitable output device or alarm, for providing an indication of high temperature based on the energy balance.

Figure 2:
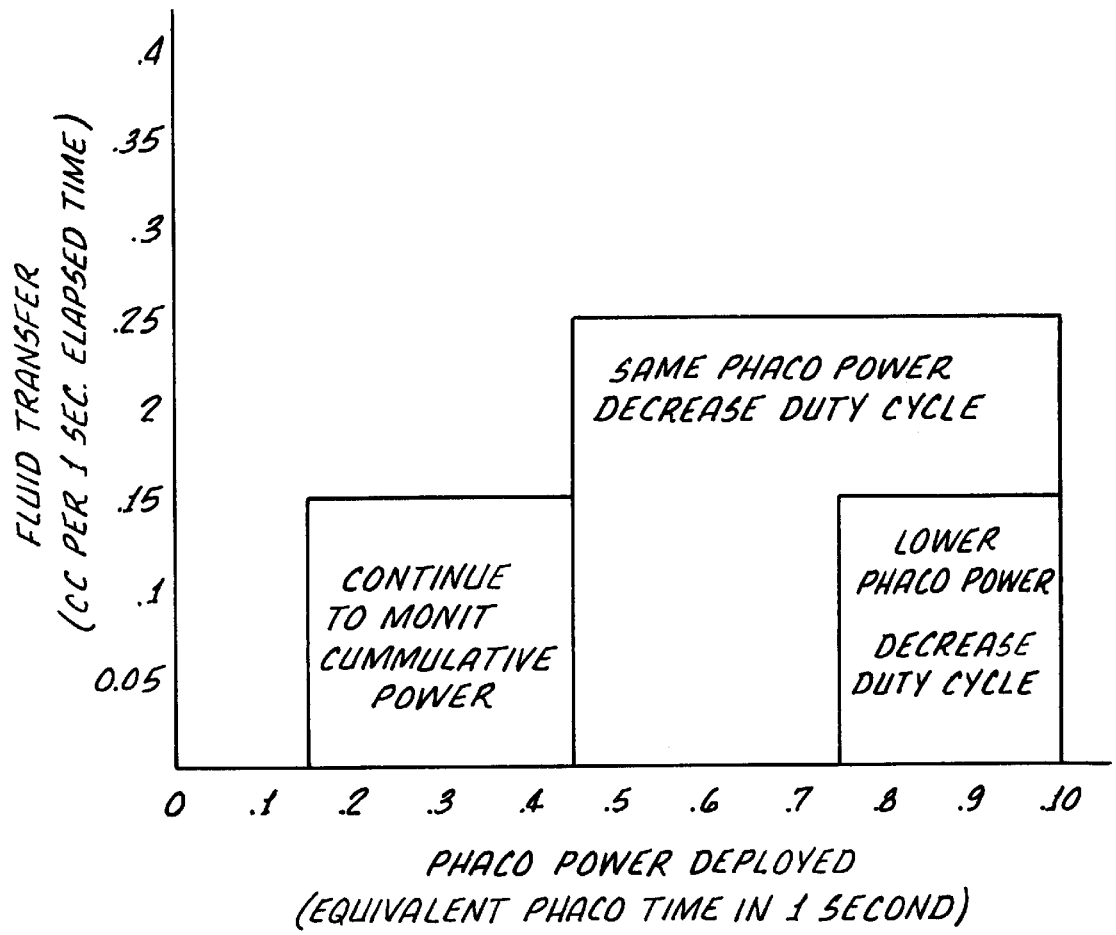
FIG. 2 is a plot of fluid transfer as a function of Phaco power displayed during a phacoemulsification procedure.

An example of a heat factor determination with corresponding system response is shown in FIG. 2, which represents an algorithm for handpiece 14 operation.

Several methods may be utilized to determine the heat factor including mathematical algorithm or a look-up table contained within system memory. FIG. 2 illustrates one way in which a heat factor may be determined from a two dimensional matrix. FIG. 2 also demonstrates one example of how a system may be programmed to respond based upon the determined heat factor within this two dimensional matrix.

A combination of change in phaco power as well as duty cycle is shown as a response to ultrasonic power and fluid transfer within a given increment of time. By monitoring the fluid removed from the eye by the aspiration means utilizing a microprocessor, the quantity of fluid capable of transferring heat away from the eye in a given increment of time can be determined or approximated. In addition, the system 10 is also capable of monitoring the cumulative ultrasonic energy deployed into the eye 16 in a given increment of time by utilizing a microprocessor 22 to either calculate energy directly from the power level utilized by the surgeon via footpedal control, not shown, or by monitoring equivalent phaco time. Equivalent phaco time is the average percent power setting on the system used by the surgeon divided by 100. Heat generation within the eye 16 is a function of the energy deployed. In response to these two calculations, a coordinate is determined within the two dimensional matrix. The system 10 response to this coordinate is either provided pre-programmed into the system or determined by the surgeon and programmed and/or modified in either a pre-operative or inter-operative manner.

The equivalent time set forth in FIG. 2 corresponds to full duty cycle of one second. That is, if the handpiece 14 is powered at one-half duty cycle, then the active time would be 2 sec., corresponding to an equivalent time of 1 sec. full duty cycle.

Although there has been hereinabove described controlled apparatus in accordance with the present invention, for the purpose of illustrating the manner in which the invention is used to advantage, it should be appreciated that the invention is not limited thereto. Accordingly, any and all modifications, variations or equivalent arrangements which may occur to those skilled in the art, should be considered to be within the scope of the present invention as defined in the appended claims.

What is claimed is:

1. In a control console for providing irrigation fluid and energy to an ultrasonic phacoemulsification handpiece and aspirating fluid from an eye during ocular surgery, control apparatus for regulating fluid flow and power, said control apparatus comprising:

means for monitoring energy provided to the handpiece by the control console;

means for monitoring energy removed from the eye by aspirated fluid; and computer means, responsive to input from the means for monitoring energy provided to the handpiece and the means for monitoring energy removed from the eye, for regulating the energy provided to the handpiece.

2. The control apparatus according to claim 1 wherein the means for monitoring energy removed from the eye includes means for measuring a flow rate of the aspirated fluid.

3. The control apparatus according to claim 1 wherein the control means includes means for regulating the duty cycle of power provided to the handpiece.

4. Control apparatus for providing fluid and power to an ultrasonic phacoemulsification handpiece during ocular surgery on an eye, said control apparatus comprising:

means for monitoring energy provided to the handpiece;

means for monitoring energy removed from the eye; and computer means, responsive to input from the means for monitoring energy provided and the means for monitoring energy removed, for calculating an energy balance over a time interval and regulating the power and fluid provided to the handpiece.

5. The control apparatus according to claim 4 further comprising means for providing irrigation fluid to the handpiece and means for aspirating fluid from the eye.

6. The control apparatus according to claim 5 wherein the means for monitoring energy removed from the eye includes means for measuring a flow rate of the aspirated fluid.

7. The control apparatus according to claim 4 wherein the computer means includes means for regulating the duty cycle of power provided to the handpiece.

8. In a control console for providing irrigation fluid and energy to an ultrasonic phacoemulsification handpiece and aspirating fluid from an eye during ocular surgery, control apparatus for regulating fluid flow and power, said control apparatus comprising:

sensor means for monitoring energy provided to the handpiece by the control console;

sensor means for monitoring energy removed from the eye; and computer means, responsive to input from the means for monitoring energy provided and the means for monitoring energy removed, for regulating the energy provided to the handpiece, and regulating fluid flow of the irrigation fluid and aspirated fluid.

9. The control apparatus according to claim 8 wherein the means for monitoring energy removed from the eye includes means for measuring a flow rate of the aspirated fluid.

10. In a control console for providing irrigation fluid and energy to an ultrasonic phacoemulsification handpiece and aspirating fluid from an eye during ocular surgery, control apparatus for regulating fluid flow and power, said control apparatus comprising:

sensor means for monitoring energy provided to the handpiece by the control console;

sensor means for monitoring energy removed from the eye by aspirated fluid; and computer means, responsive to input from the means for monitoring energy provided to the handpiece and the means for monitoring energy removed from the eye, for regulating the energy provided to the handpiece.

11. Control apparatus for providing fluid and power to an ultrasonic phacoemulsification handpiece during ocular surgery on an eye, said control apparatus comprising:

sensor means for monitoring energy provided to the handpiece;

sensor means for monitoring energy removed from the eye; and computer means, responsive to input from the means for monitoring energy provided and the means for monitoring energy removed, for calculating an energy balance over a time interval and regulating the power and fluid provided to the handpiece.

12. In a control console for providing irrigation fluid and energy to an ultrasonic phacoemulsification handpiece and aspirating fluid from an eye during ocular surgery, control apparatus for regulating fluid flow and power, said control apparatus comprising:

sensor means for monitoring energy provided to the handpiece by the control console;

sensor means for monitoring energy removed from the eye; and computer means, responsive to input from the means for monitoring energy provided and the means for monitoring energy removed, for regulating the energy provided to the handpiece, and regulating fluid flow of the irrigation fluid and aspirated fluid.

* * * * *